(12) United States Patent
Kiani et al.

(10) Patent No.: US 7,753,095 B2
(45) Date of Patent: Jul. 13, 2010

(54) STORING AND HANDLING LIQUID REAGENTS

(75) Inventors: Sepehr Kiani, Watertown, MA (US); John Kepler, Lexington, MA (US)

(73) Assignee: Helicos Biosciences Corporation, Cambridge, MA (US)

( * ) Notice: Subject to any disclaimer, the term of this patent is extended or adjusted under 35 U.S.C. 154(b) by 566 days.

(21) Appl. No.: 11/640,000

(22) Filed: Dec. 15, 2006

(65) Prior Publication Data

US 2008/0142113 A1 Jun. 19, 2008

(51) Int. Cl.
*B65B 1/04* (2006.01)
(52) U.S. Cl. ........................................ 141/330; 141/285
(58) Field of Classification Search ................ 141/329, 141/330, 285, 346, 351; 422/100, 102
See application file for complete search history.

(56) References Cited

U.S. PATENT DOCUMENTS

| | | | |
|---|---|---|---|
| 3,991,627 A | 11/1976 | Laird et al. | |
| 4,684,365 A * | 8/1987 | Reinicke | 604/126 |
| 5,031,797 A | 7/1991 | Boris et al. | |
| 5,329,976 A * | 7/1994 | Haber et al. | 141/25 |
| 6,110,428 A | 8/2000 | Borst et al. | |
| 2003/0175157 A1* | 9/2003 | Micklash et al. | 422/70 |
| 2004/0164092 A1 | 8/2004 | DiLeo | |
| 2006/0133955 A1 | 6/2006 | Peters | |
| 2006/0153743 A1 | 7/2006 | Blomsma et al. | |

OTHER PUBLICATIONS

International Search Report (ISR) for international application No. PCT/2007/087126 corresponding to U.S. Appl. No. 11/640,000, May 16, 2008 (1 pg.).
Written Opinion of the International Searching Authority for international application No. PCT/2007/087126 corresponding to U.S. Appl. No. 11/640,000, May 16, 2008 (5 pgs.).

* cited by examiner

*Primary Examiner*—Gregory L Huson
*Assistant Examiner*—Jason K Niesz
(74) *Attorney, Agent, or Firm*—Thomas Meyers; Adam Schoen; Brown Rudnick LLP

(57) ABSTRACT

A liquid storage apparatus provides a safe and easy to use device for efficiently managing liquid reagents used in a variety of laboratory equipment. The liquid storage apparatus helps reduce the likelihood of accidental sticks to laboratory personnel, allows for flexibility of experimental design, and helps maximize the use of chemical regents to prevent waste. The apparatus includes a plurality of containers of liquid with a pierceable septum interface at each end. The apparatus also includes a lower array of needles with each of the lower needles in the lower array of needles arranged to penetrate the bottom pierceable septum of a different one of the containers. Each of the needles includes a passage so the liquid can flow out of the pierced container. The apparatus further includes an upper array of needles with each of the upper needles in the upper array of needles arranged to penetrate the top pierceable septum of a different one of the containers. Each of the needles include a passage so gas can flow into the pierced container to occupy the space created as the liquid flows out of the container.

10 Claims, 12 Drawing Sheets

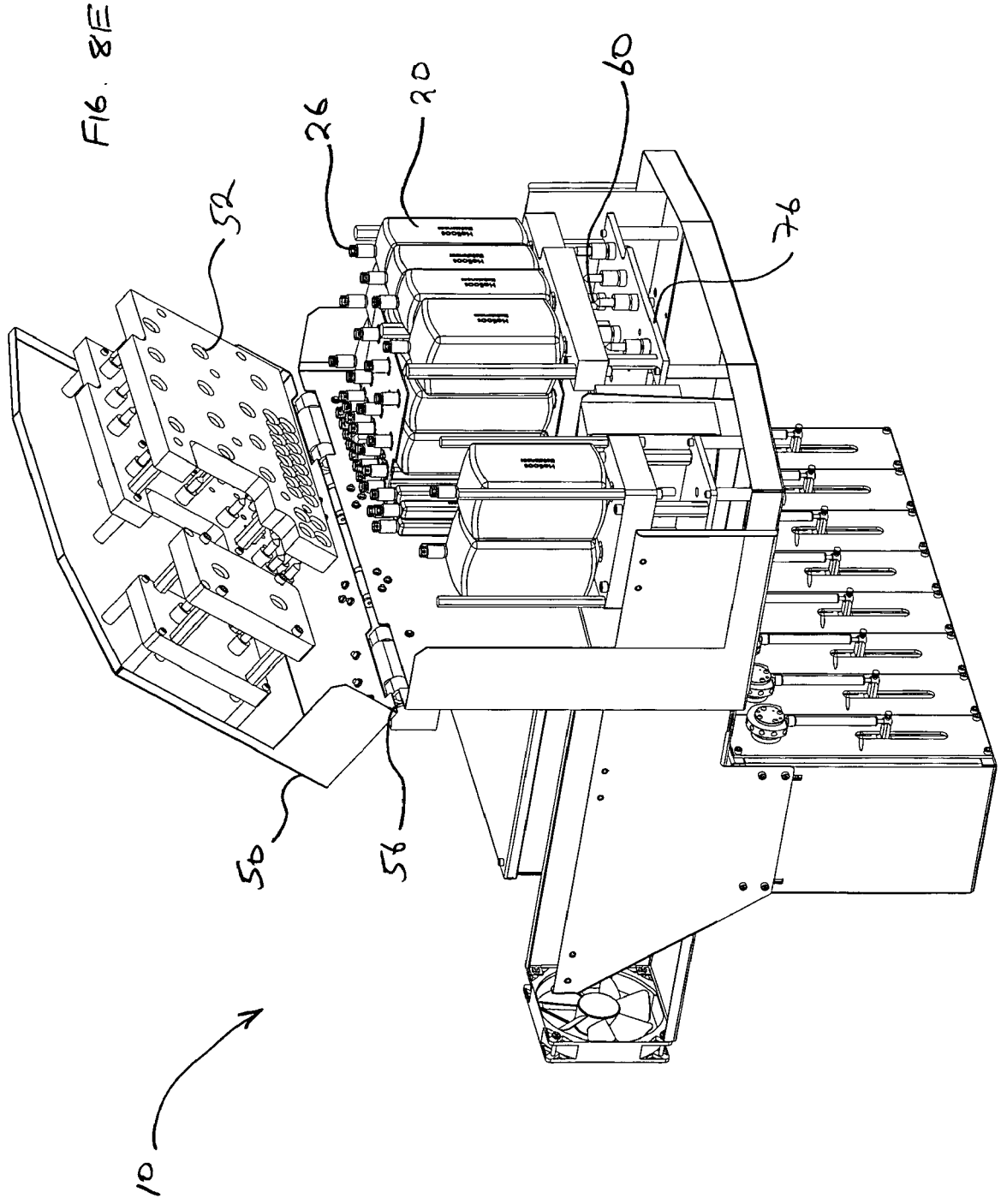

STORING AND HANDLING LIQUID REAGENTS

TECHNICAL FIELD

The invention relates generally to storing and handling liquid reagents for use in single molecule sequencing.

BACKGROUND INFORMATION

Fluidic systems are used in a variety of areas including biochemical analysis, medical diagnostics, analytical chemistry, chemical synthesis, and environmental monitoring. Microfluidic systems provide certain advantages in acquiring chemical and biological information. For example, microfluidic systems permit complicated processes to be carried out using small amounts of reagents.

In certain diagnostic equipment and systems, large numbers of various sized bottles of different liquid reagents are required. In these systems, liquids are typically stored in conventional bottles with a needle pierceable septum at one end. Fluids can be extracted from these bottles in several ways. For example, the septum can be pierced with a short or a long needle. The long needle is designed to reach the bottom of the bottle to extract the liquid, and the short needle provides an air vent to replace the liquid with air as it is extracted from the bottle. A long needle causes safety concerns and requires complex mechanisms to protect and guide into the bottle. Another example of a method for extracting the liquid from these bottles is to provide a significant air volume above the liquid to allow for low vacuum level build-up while extracting. This method has certain drawbacks as well because allowing even a small vacuum build-up in the bottle can introduce dispensing errors at selector valves in the liquid handling system. Furthermore, liquid storage systems and interfaces that use this method are difficult to manage.

SUMMARY OF THE INVENTION

The present invention provides for liquid reagent storage and handling and can be used in conjunction with microfluidic volume analyzing equipment such as chemical analyzers and single molecule sequencing equipment. Generally, the invention provides a safe and easy way to manage efficiently liquid reagents for use in a variety of laboratory equipment. The present invention helps reduce the likelihood of accidental sticks to laboratory personnel, allows for flexibility of experimental design, and helps maximize the use of chemical reagents to prevent waste.

In a particular embodiment, the invention features an apparatus comprising a plurality of containers. Each of the containers includes a liquid reagent, a top pierceable septum and a bottom pierceable septum. The apparatus also includes a lower array of needles. Each of the lower needles in the lower array of needles is arranged to penetrate the bottom pierceable septum of a different one of the containers and each of the needles include a passage so the liquid can flow out of the pierced container. The apparatus further includes an upper array of needles. Each of the upper needles in the upper array of needles is arranged to penetrate the top pierceable septum of a different one of the containers and each of the needles include a passage so gas can flow into the pierced container to occupy the space created as the liquid flows out of the container.

In an alternative embodiment, a subset of two or more of the containers can be selectively secured together to form a cartridge assembly. One of more of these cartridge assemblies can be used to streamline or simplify the process of loading and unloading liquid reagents. A further aspect of this embodiment allows for customized cartridge assemblies designed for specific applications so that the liquid in each container of the cartridge is used up at approximately the same time.

In another aspect of the invention, the lower array of needles includes non-coring needles with a closed sharpened end. These needles include an aperture in the side of the needle, which can be positioned slightly inside the bottom pierceable septum to maximize the utilization of the liquid reagents.

In a further aspect of the invention, the upper array of needles is fluidly coupled to a filter, ventilation system, check valve or an inert gas system. For a variety of reasons it may be important to regulate the flow of gas into, or out of the containers as the liquids are being withdrawn. Some reagents may give off toxic fumes or unpleasant odors while others may degrade in the presence of oxygen. Providing a partially or completely sealed system can help provide a safer work environment and prevent the liquid reagents from breaking down or altering their composition.

In yet another aspect of the invention, the liquid storage apparatus further includes a liquid level sensor. Analytical equipment utilizing the liquid reagents stored in the apparatus can be damaged if gasses are allowed to enter the other systems. One way of preventing this damage is to provide liquid level sensors for each individual container or for the entire apparatus that either notifies the user when the liquid level is getting low or shuts down the equipment. Various types of sensors can be used with the apparatus including, for example, ultrasonic, optical, capacitance level sensing.

BRIEF DESCRIPTION OF THE DRAWINGS

For a fuller understanding of how to make and use a needle and container arrangement according to the invention, reference is made to the following description which should be taken in conjunction with the accompanying drawing figures wherein like reference characters denote corresponding parts throughout the several views and wherein:

FIG. 8E is a schematic view of the needle and container assembly of FIG. 8C showing the cover in an opened position.

DESCRIPTION

Embodiments of the present invention are described below. It is, however, expressly noted that the present invention is not limited just to these disclosed embodiments. Various modifications not specifically detailed are within the scope of this disclosure. All relative descriptions herein such as top, bottom, left, right, up, and down are with reference to the figures, and thus should not be construed in a limiting sense. The present invention can be applied to storing and handling liquids for many types of analytical equipment, such as, for example, flow cytometers and chemical analyzers. Further, the disclosed liquid storage/handling apparatus can be used as part of a system for detecting single molecules by, for example, optical detection of single nucleotides.

Embodiments of a fluidic apparatus according to the present invention generally streamline the analysis of biochemical assays. Each of the embodiments enables simple and safe loading and unloading of reagent containers, allow for more accurate discharge of reagent volumes, and maximizes the utilization of the liquid volume in each individual container.

Figure 1:
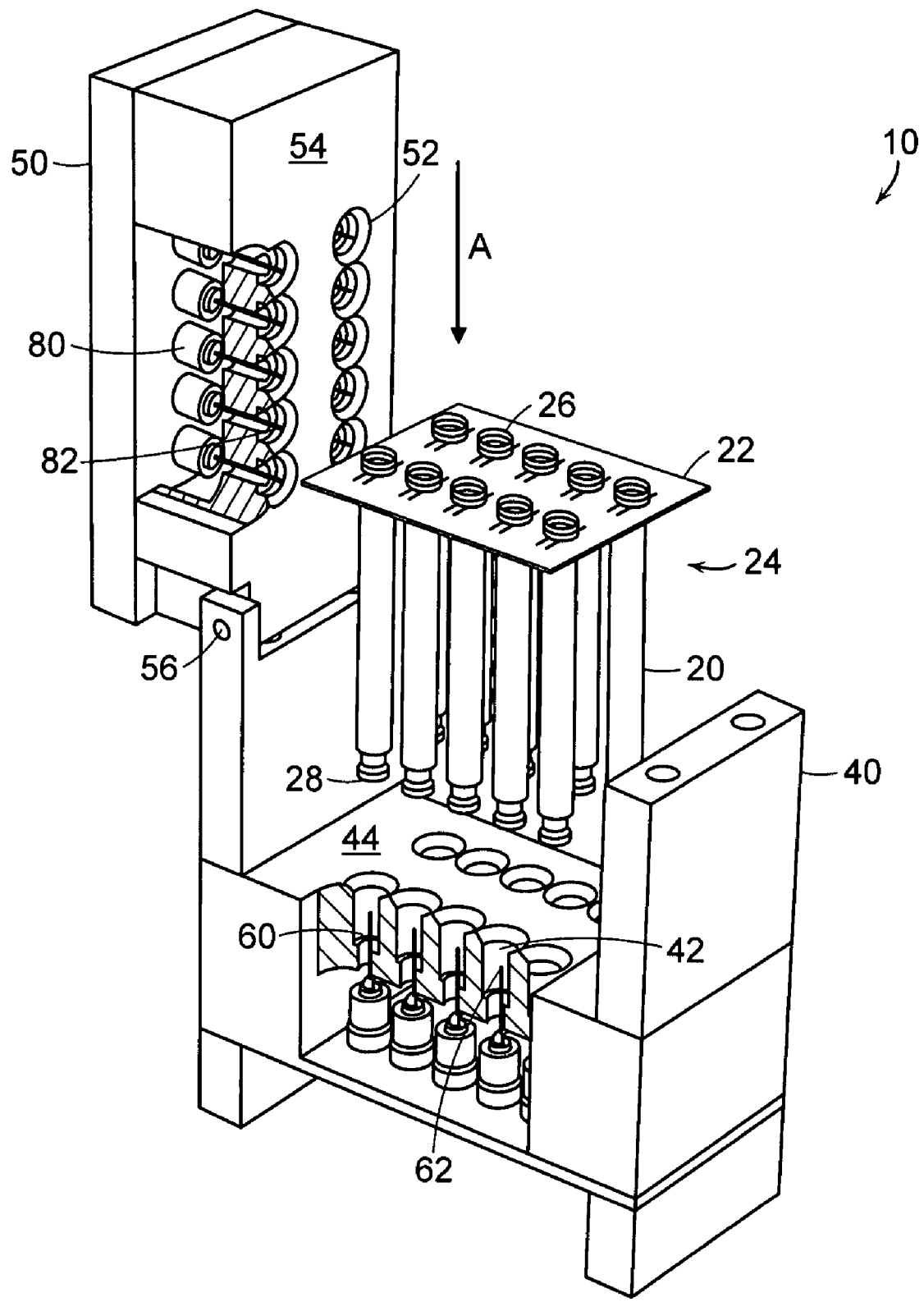
FIG. 1 is a schematic perspective view of an exemplary embodiment of a needle and container arrangement showing the containers in the process of being loaded.

In the embodiment depicted in FIG. 1, the liquid storage apparatus 10 includes a plurality of containers 20 filled with liquid reagents being loaded into a frame 40. The containers 20 are selectively secured to a tray carrier 22 thereby forming a cartridge assembly 24. Other means for arranging the plurality of containers 20 into a unitary cartridge assembly 24 will be apparent to one skilled in the art. In alternative embodiments, the containers 20 can be loaded into the frame 40 individually or in multiple cartridge assemblies. The containers 20 can be glass or a suitable plastic material such as acrylic, polycarbonate, or polypropylene. In some embodiments, the materials used in each container 20 can be the same or different from the other containers 20 depending on the liquid being stored, such that the liquid is not reactive with the container 20 material. Also, individual liquids may need to be stored in different thermal or atmospheric conditions and therefore thermal expansion characteristics may be an important consideration when selecting the container material.

Each container 20 includes a top pierceable septum 26 and a bottom pierceable septum 28. These septa 26, 28 can be made from any pliable material that allows penetration by a needle and then seals the outside periphery of the needle to prevent leakage. Examples of such materials are polytetrafluoroethylene (PTFE), fluorinated ethylene-propylene (FEP) and perfluoroalkoxy polymer resin (PFA), which are all generally known by DuPont's brand name Teflon®. The septa 26, 28 can be the same or different depending on the desired application and/or the liquid being stored in each container. The septa 26, 28 can be secured to the container 20 in any of a number of ways including, for example, snap on, screw cap, mechanically fastened, heat welding, vibration welding, ultrasonically welding, or bonding with an adhesive.

The liquid storage apparatus also includes a lower array of needles 60. Each of the needles of the lower array of needles 60 is disposed in a cavity 42 recessed into the bottom surface 44 of the frame 40. As the containers 20 of the cartridge assembly 24 are being lowered into the frame 40 in the direction indicated by line A, the bottom pierceable septa 28 are received into the cavities 42. The cavities 42 can be slightly tapered with the widest part at the bottom surface 44 of the frame 40 to help guide the containers 20 into the cavities 42. The needles 60 are disposed in the cavities 42 such that the points 62 of the needles 60 are below the bottom surface 44 of the frame 40 to help prevent accidental sticks. The cavities 42 also help ensure proper alignment of the needles 60 in the center of each septum 28 prior to penetration.

Figure 2A:
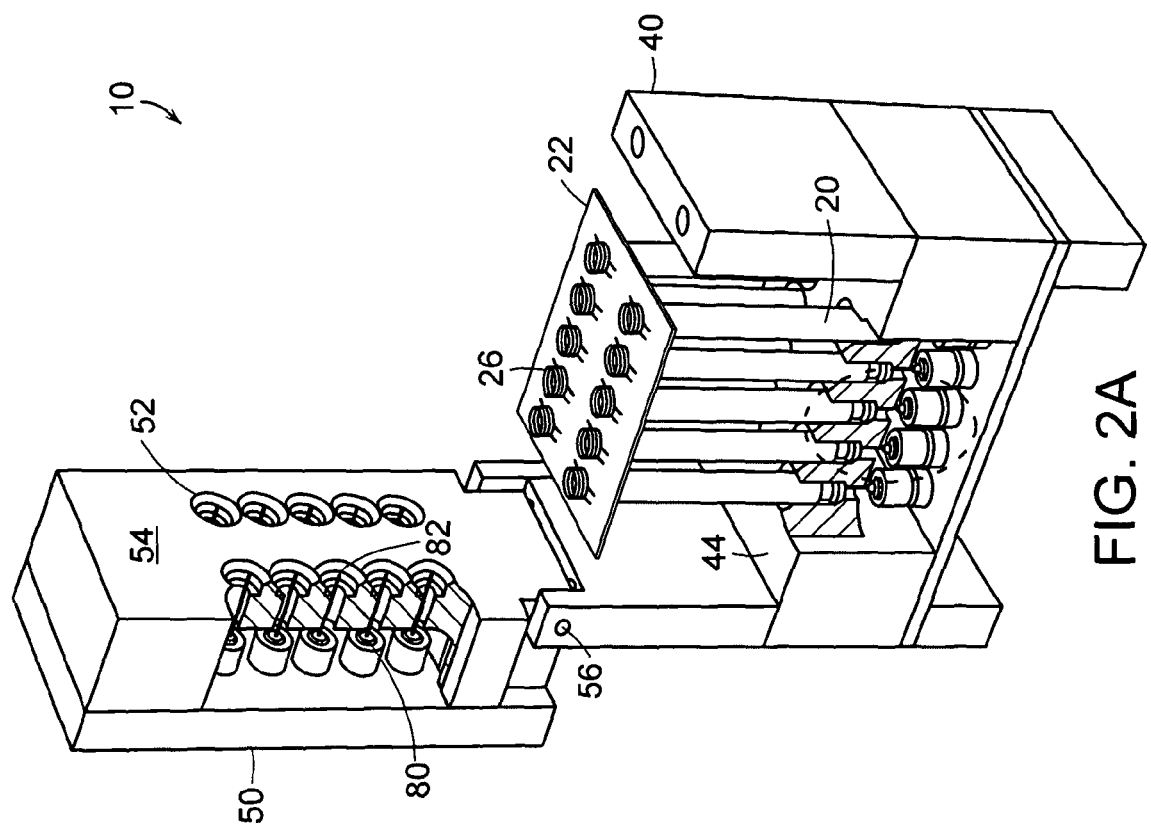
FIG. 2A is a schematic perspective view of the needle and container arrangement of FIG. 1 showing the containers in the loaded position.
Figure 2B:
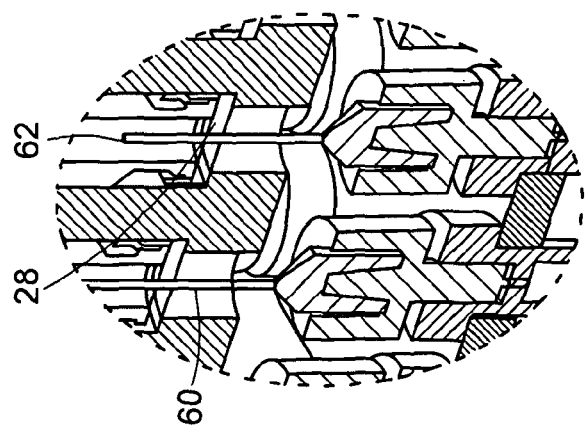
FIG. 2B is an enlarged schematic perspective view of the needle and container arrangement of FIG. 2A showing the lower needles pierced through the bottom pierceable septum of two of the containers.

Referring now to FIGS. 2A and 2B, the containers 20 are shown partially loaded into the frame 40. Each of the needles in the lower array needles 60 has pierced the bottom pierceable septum 28 of each of the containers 20 and is penetrating into the liquid reagent. Each needle in the lower array of needles 60 has a passage allowing the liquid reagent in the pierced container 20 to flow out of the container 20.

Figure 3A:
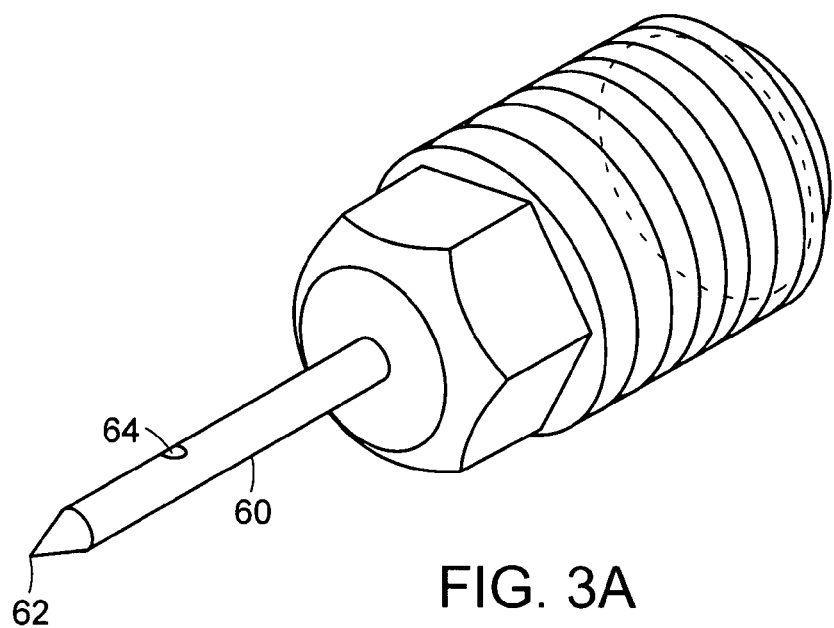
FIG. 3A is a schematic perspective view of a Trocar needle for use in the lower array of needles of the needle and container arrangement of FIG. 1.
Figure 3B:
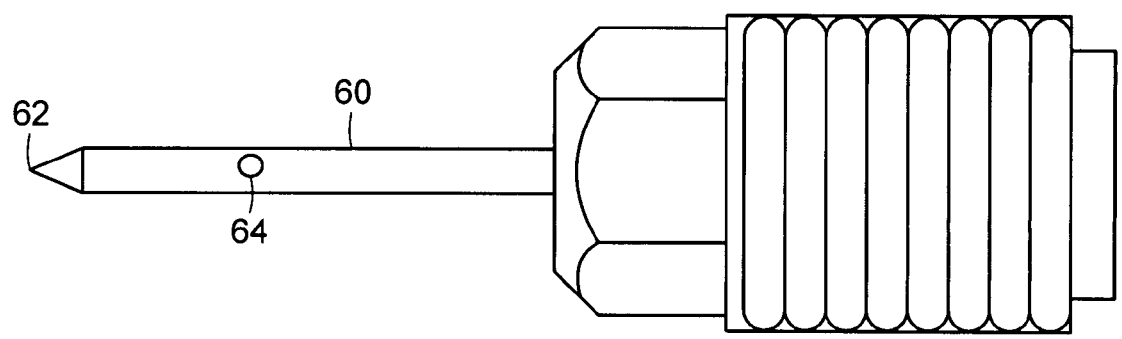
FIG. 3B is a schematic front view of the Trocar needle shown in FIG. 3A.

The liquid reagents used in certain analytical procedures are very expensive and therefore it is desirable to use as much of the liquid volume as possible to prevent waste. Referring now to FIGS. 3A and 3B, a Trocar needle for use in the lower array of needles 60 is shown. In this embodiment, the needle 60 has a closed sharpened point 62 and an aperture 64 in the side such. These Trocar needles with a side aperture 64 allow the point 62 of the needle 60 to protrude into the container a sufficient distance to pierce the septum 28, while also providing the outlet for the liquid near the septum 28. This allows for a maximum amount of the liquid volume from each container 20 to be utilized. In alternative embodiments, the needles in the lower array of needles 60 can be any type of needle including, for example, a thoracentesis needles, Veress needles, or Huber needles. The needles 60 can be fabricated from stainless steel, titanium or other similarly rigid material in a range of sizes and lengths depending on the requirements of a particular application.

The liquid storage apparatus also includes an upper array of needles 80. Each of the needles of the upper array of needles 80 is disposed in a cavity 52 recessed into the bottom surface 54 of a cover 50. The cover 50 is pivotally attached to the frame 40 with a hinge 56. The cavities 52 can be slightly tapered with the widest part at the bottom surface 54 of the cover 50 to help guide the containers 20 into the cavities 52. The needles 80 are disposed in the cavities 52 such that the points 82 of the needles 80 are below the bottom surface 54 of the cover 50. These cavities 52 are similar to the cavities 42 described above in relation to the frame 40 and perform substantially the same function, such as prevention of accidental sticks and ensuring proper alignment of the needles 80 in the center of each upper septum 26 prior to penetration.

Figure 4A:
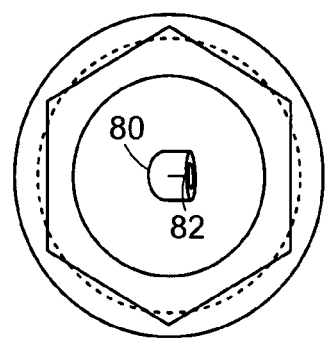
FIG. 4A is a schematic top view of a deflected tip needle for use in the upper array of needles of the needle and container arrangement of FIG. 1.
Figure 4B:
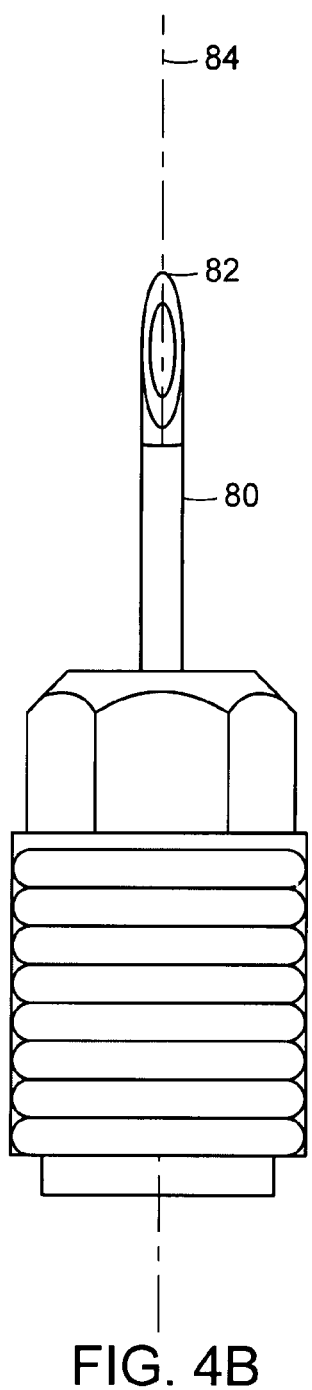
FIG. 4B is a schematic front view of the deflected tip needle shown in FIG. 4A.
Figure 4C:
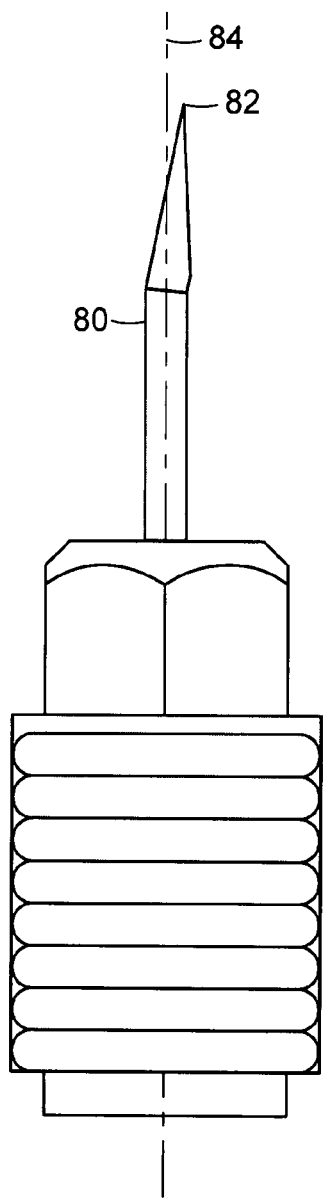
FIG. 4C is a schematic side view of the deflected tip needles shown in FIG. 4A.

Referring now to FIGS. 4A-4C, a deflected tip needle of the upper array of needles 80 is shown. In the deflected tip needle 80, the sharpened point 82 is slightly bent or offset from the longitudinal axis 84 of the needle 80. This deflected tip design provides a needle that is non-coring such that as the top pierceable septum 26 is pierced, none of the septum 26 material is removed, which could potentially cause obstructions in the apparatus 10 or microfluidic system. In alternative embodiments, the upper needles 80 can be any type of needle including, for example, a thoracentesis needles, Veress needles, Huber needles, or Trocar needles. The needles 60 can be fabricated from stainless steel, titanium or other similarly rigid material in a range of sizes and lengths depending on the requirements of a particular application.

After a plurality of individual containers 20 or a cartridge assembly 24 has been loaded in to the frame 40, the cover 50 can be closed and the needles 80 penetrate the top pierceable septum 26. The needles in the upper array of needles 80 are relatively short so they all make contact with the top pierceable septa 26 at approximately the same time when the cover is swung shut. As described above, the cavities 54 in the cover 50 are tapered to help align the needles 80 near the center of the top pierceable septa 26 and thus no sophisticated alignment techniques or equipment is necessary. Each needle in the upper array of needles 80 has a passage allowing gas to flow into the container to occupy the space in the in the pierced container 20 created by the liquid reagent flowing out of the container 20.

Figure 5:
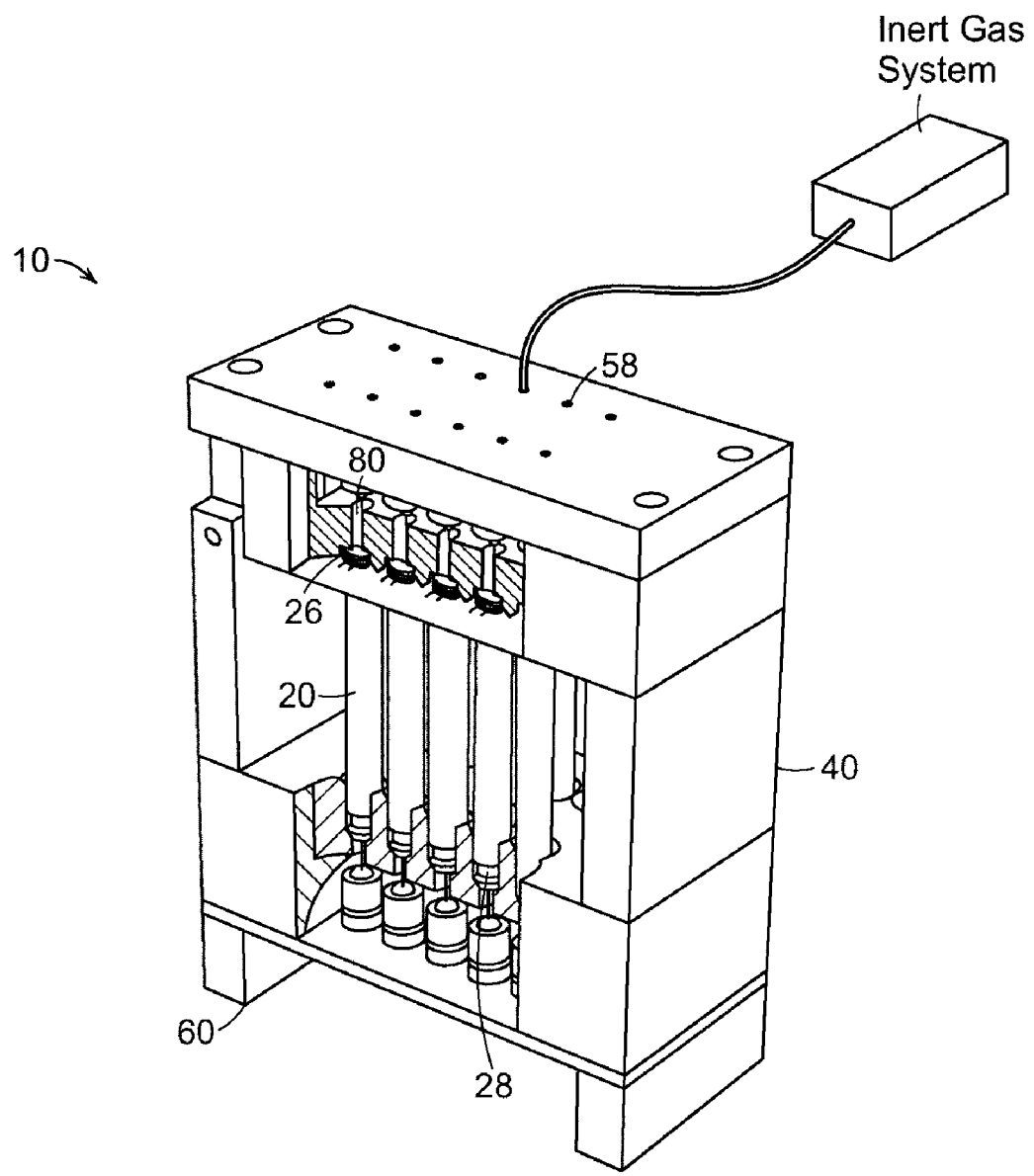
FIG. 5 is a schematic perspective view of the needle and container arrangement of FIG. 1 showing the cover in a closed position.

Referring now to FIG. 5, a fully loaded liquid storage apparatus 10 is shown. A series of air vents 58 are fluidly coupled to the passages of the needles in the upper array of needles 80, which allow direct venting of the containers 20 to the atmosphere. As the liquid reagents are withdrawn through the passages in the needles lower array of needles, air can freely enter the containers 20 through the passages in the needles of the upper array of needles 80 to replace the liquid volume as it is removed. Replacing the space occupied by the liquid with air or other gas maintains a consistent operating pressure in the containers 20, i.e., no vacuum build-up. Providing a consistent operating pressure prevents dispensing errors at selector valves in the liquid handling system.

The liquid reagents used in some microfluidic volume analyzing equipment have toxic vapors or have an unpleasant odor. In this embodiment, the air vents 58 can be fluidly coupled to a filter (not shown) such as a biological grade filter or to a laboratory ventilation system. In further embodiments, the liquids being stored may be extremely volatile in which case a one way check valve or a series of check valves may be included to allow air to flow into the containers after liquid is withdrawn In yet a further embodiment, certain reagents may be reactive with oxygen and therefore the air vents 58 may be fluidly coupled to an inert gas system to prevent the reagents from degrading.

Figure 6A:
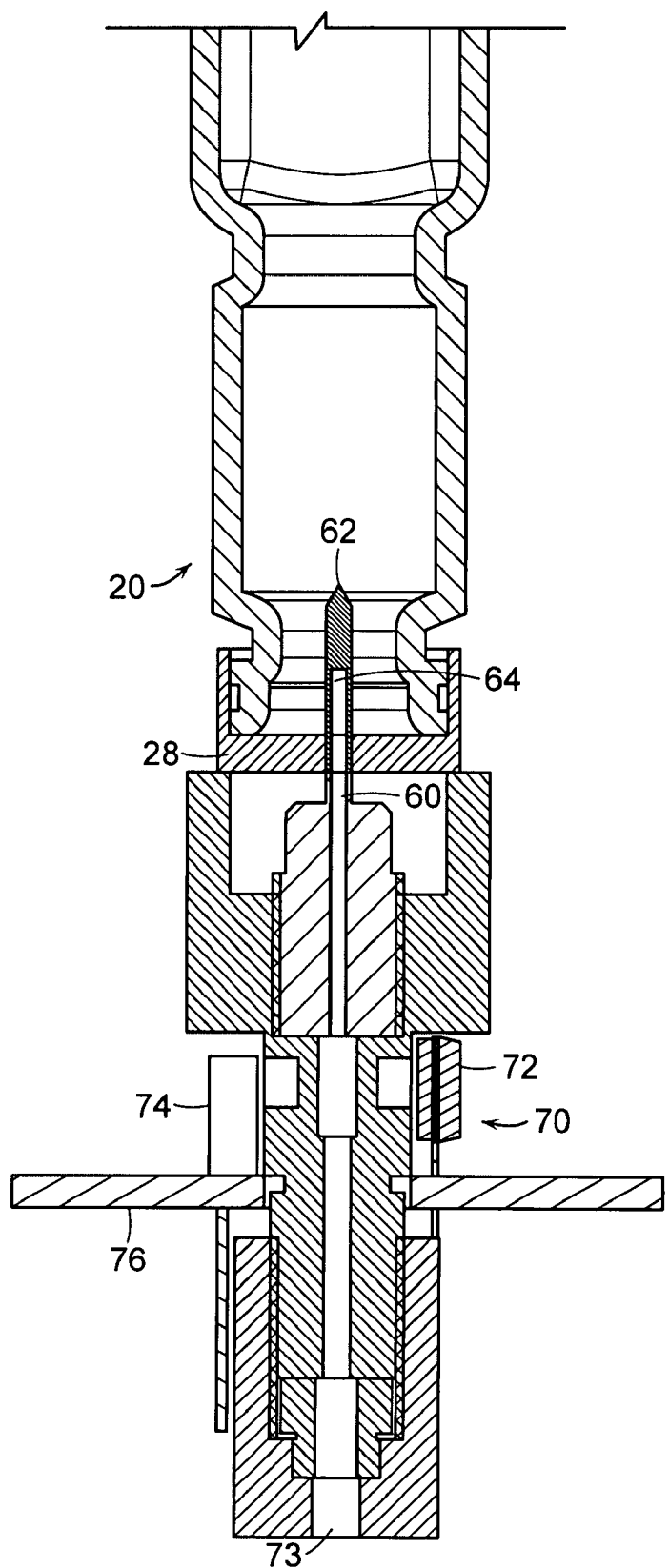
FIG. 6A is a cross-section front view of an individual container of the needle and container arrangement of FIG. 1 showing a lower needle pierced through the bottom pierceable septum.
Figure 6B:
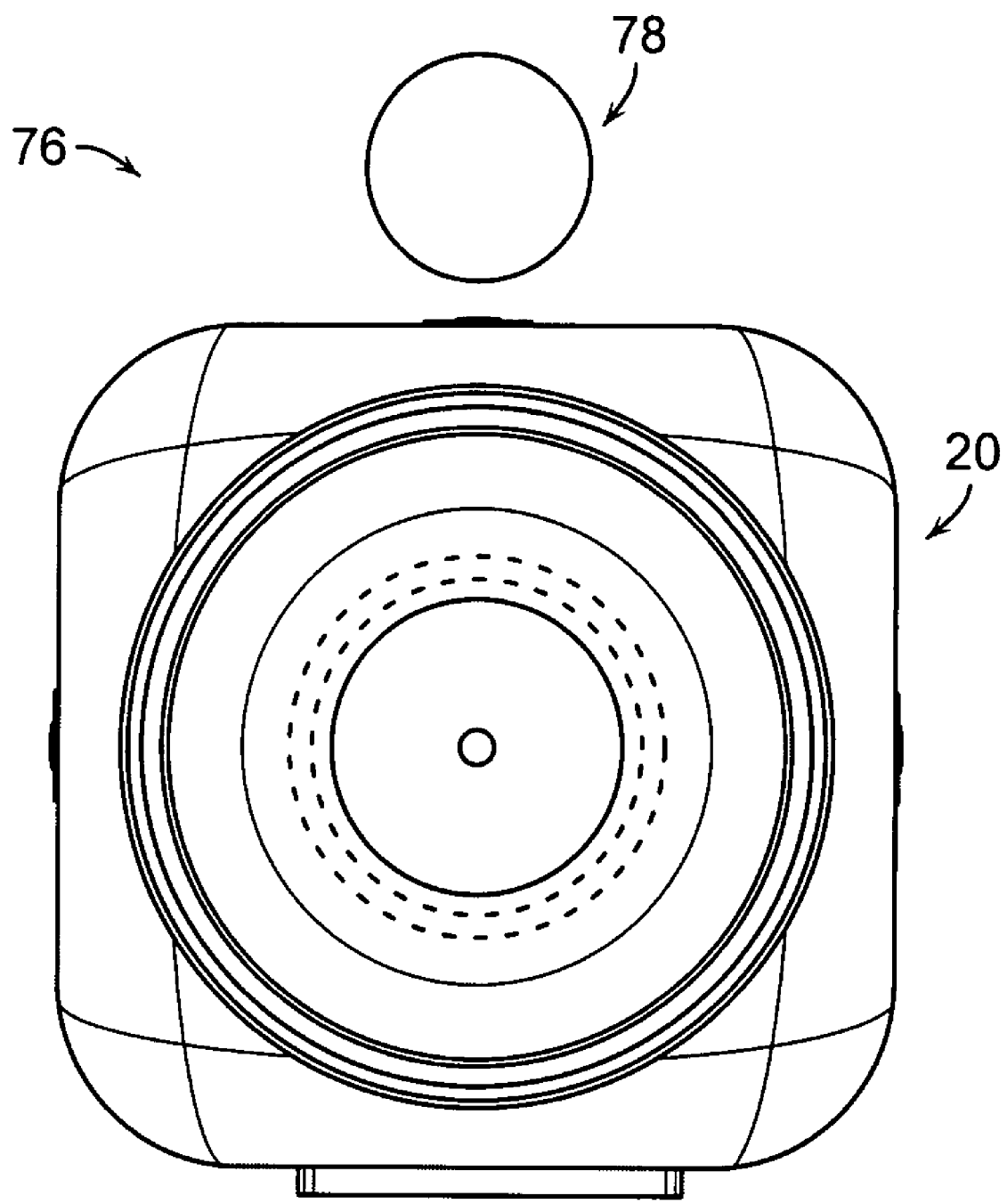
FIG. 6B is a top view of an individual container of the needle and container arrangement of FIG. 1.

Analytical equipment utilizing liquid reagents can be damaged if gasses are allowed to enter the liquid handling system. One way of preventing this damage is to provide liquid level sensors for the entire apparatus or a level sensor at each individual container. Referring now to FIGS. 6A and 6B, the liquid storage apparatus 10 further includes a liquid level sensor 70. As shown in FIG. 6A, the liquid level sensor 70 includes a photo sensor 72 and a light-emitting diode (LED) 74. The liquid level sensor 70 is positioned on a circuit board 76 below each of the containers 20 along the flow path between the aperture 64 of the lower needle 60 and the outlet 73 to the liquids handling system. The photo sensor 72 is located on the opposite side of the flow path from the LED 74. This type of liquid level sensor 70 is known as an optical level sensor and can sense the presence or absence of fluid bases on the light transmitted from the LED 74 thought the flow path. Other types of liquid level sensors that can be used with the liquid storage apparatus 10 include, for example, ultrasonic level sensors and capacitance level sensors.

The liquid level sensors can be configured to shut down the equipment when the liquid in the containers has been fully utilized or to provide notification to the user when the liquid level is either getting low or is completely empty. As shown in FIG. 6B, a LED 78 is attached to the circuit board 76 next to the container 20. The LED 78 provides a visual indication to the user when that particular container 20 is empty. The LEDs may also be configured to provide a visual indication of where certain containers 20 should be loaded for particular experimental procedures.

Figure 7:
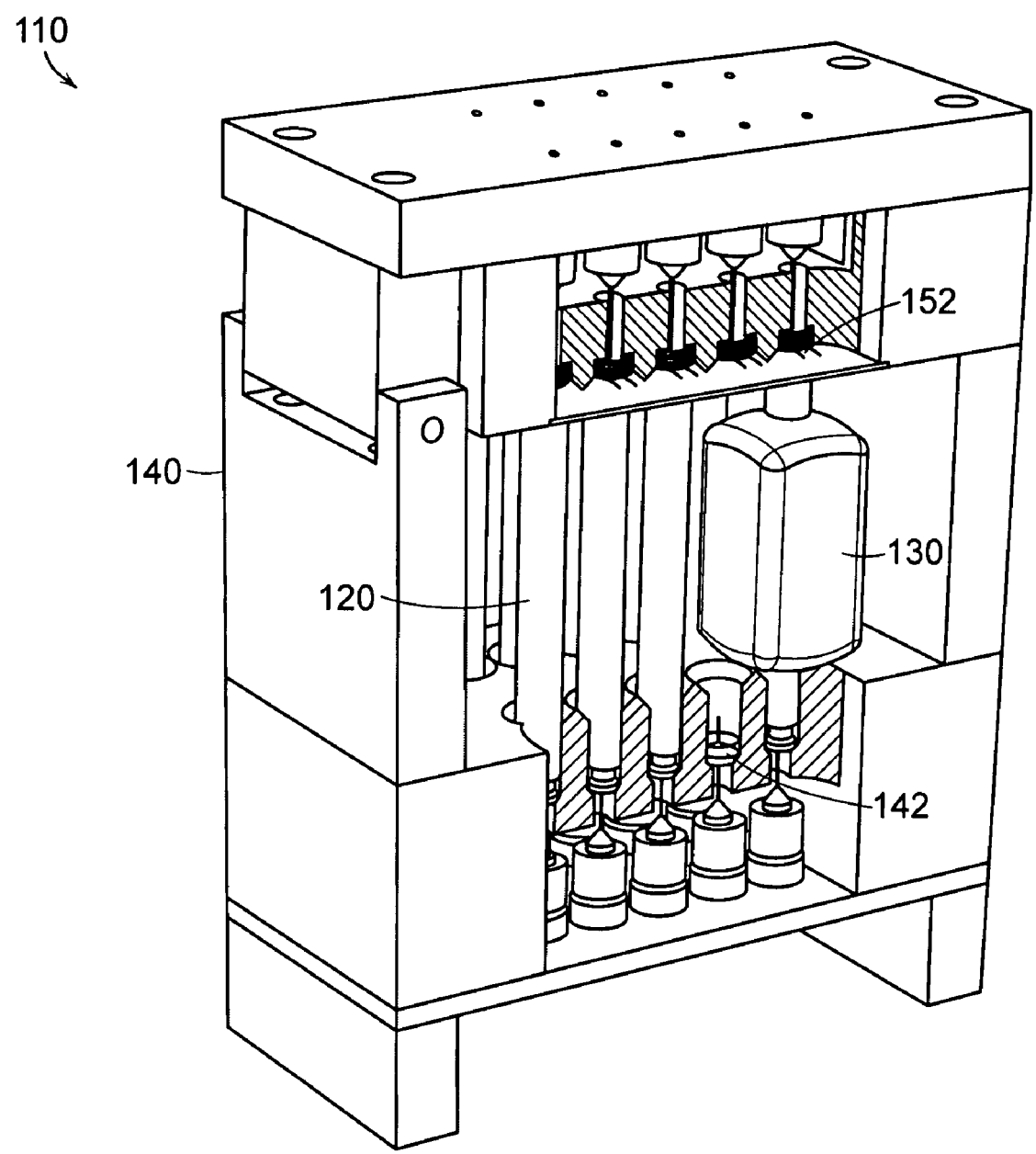
FIG. 7 is a schematic perspective view of an alternative exemplary embodiment of a needle and container arrangement with different sized containers.
Figure 8B:
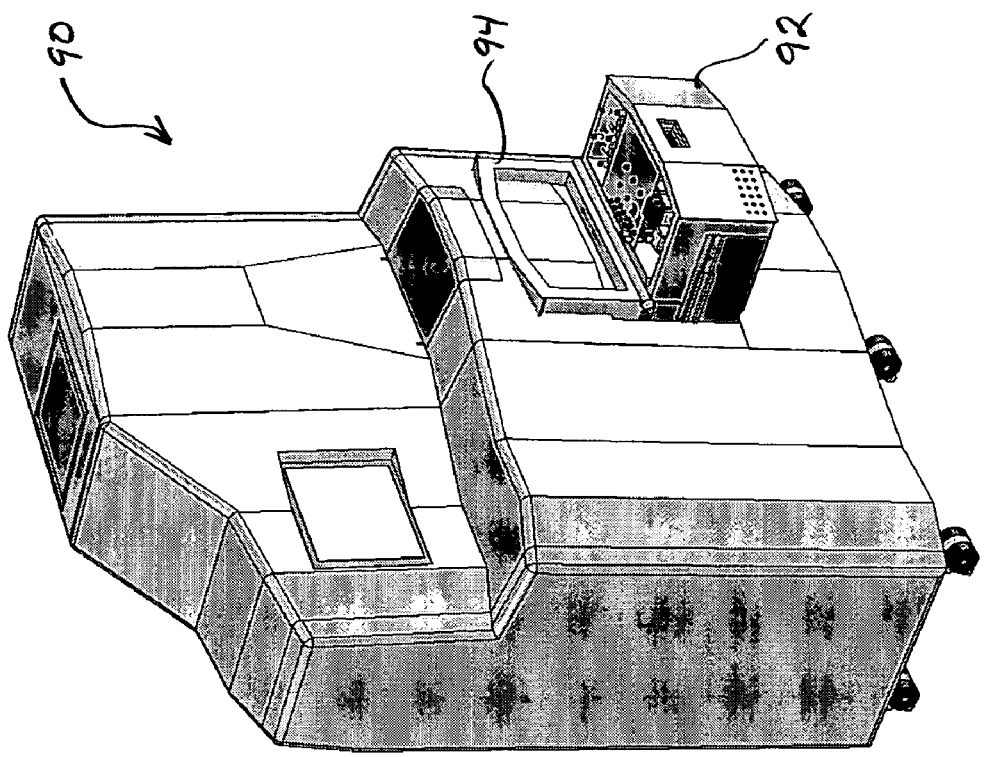
FIG. 8B is a schematic view of an apparatus that can be used to perform analytical experimentation with an exemplary embodiment of needle and container arrangement shown in FIG. 1 with its liquids compartment drawer in the open position.
Figure 8A:
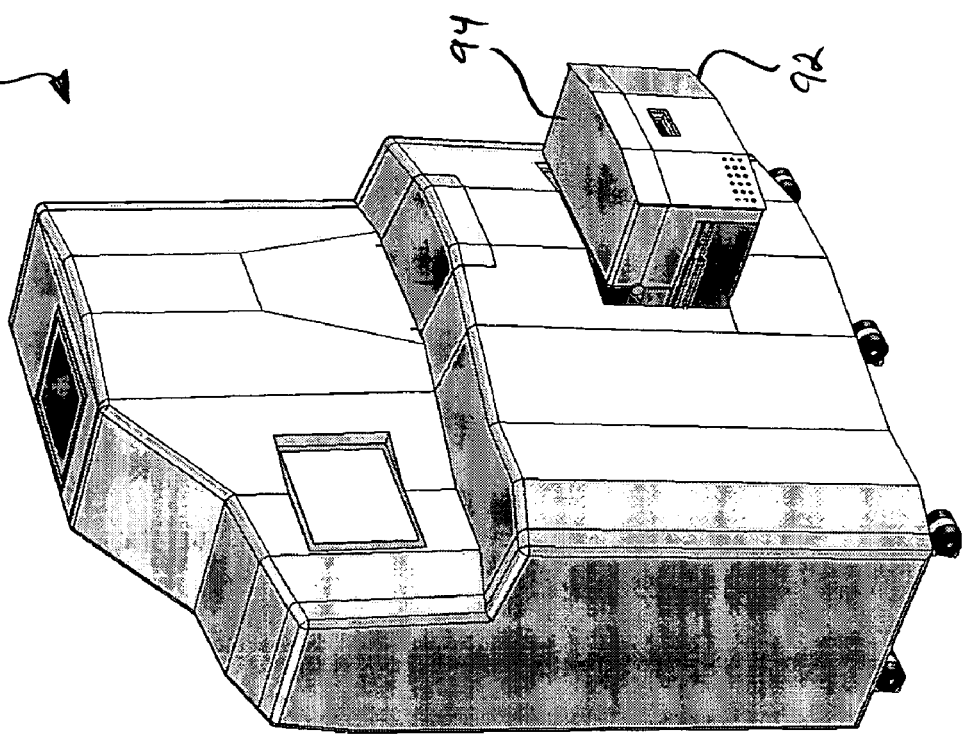
FIG. 8A is a schematic view of an apparatus that can be used to perform analytical experimentation with an exemplary embodiment of needle and container arrangement shown in FIG. 1.
Figure 8C:
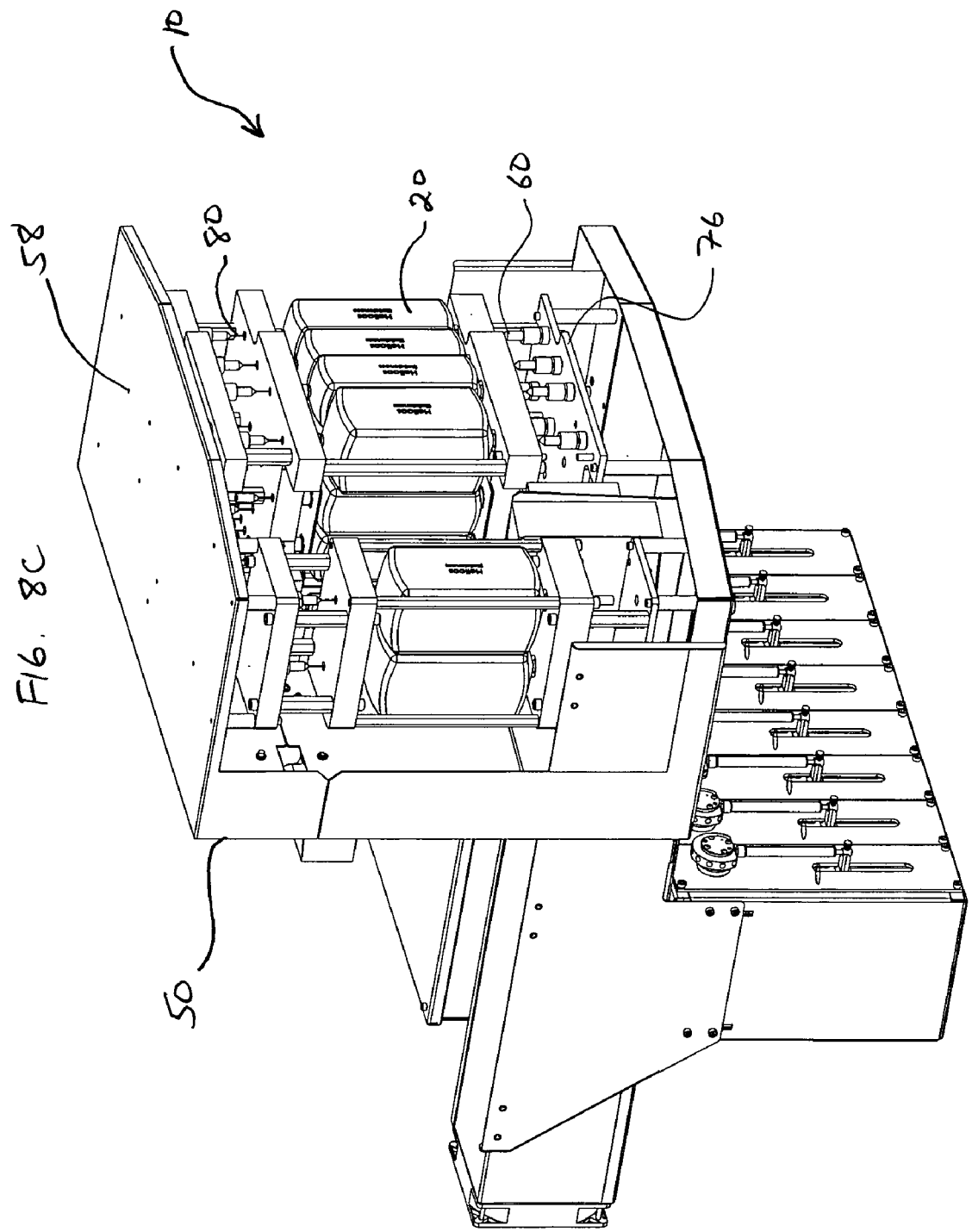
FIG. 8C is a schematic view of a needle and container assembly of FIG. 1 integrated into a liquids compartment of the apparatus used to perform analytical experimentation shown in FIGS. 8A and 8B.
Figure 8D:
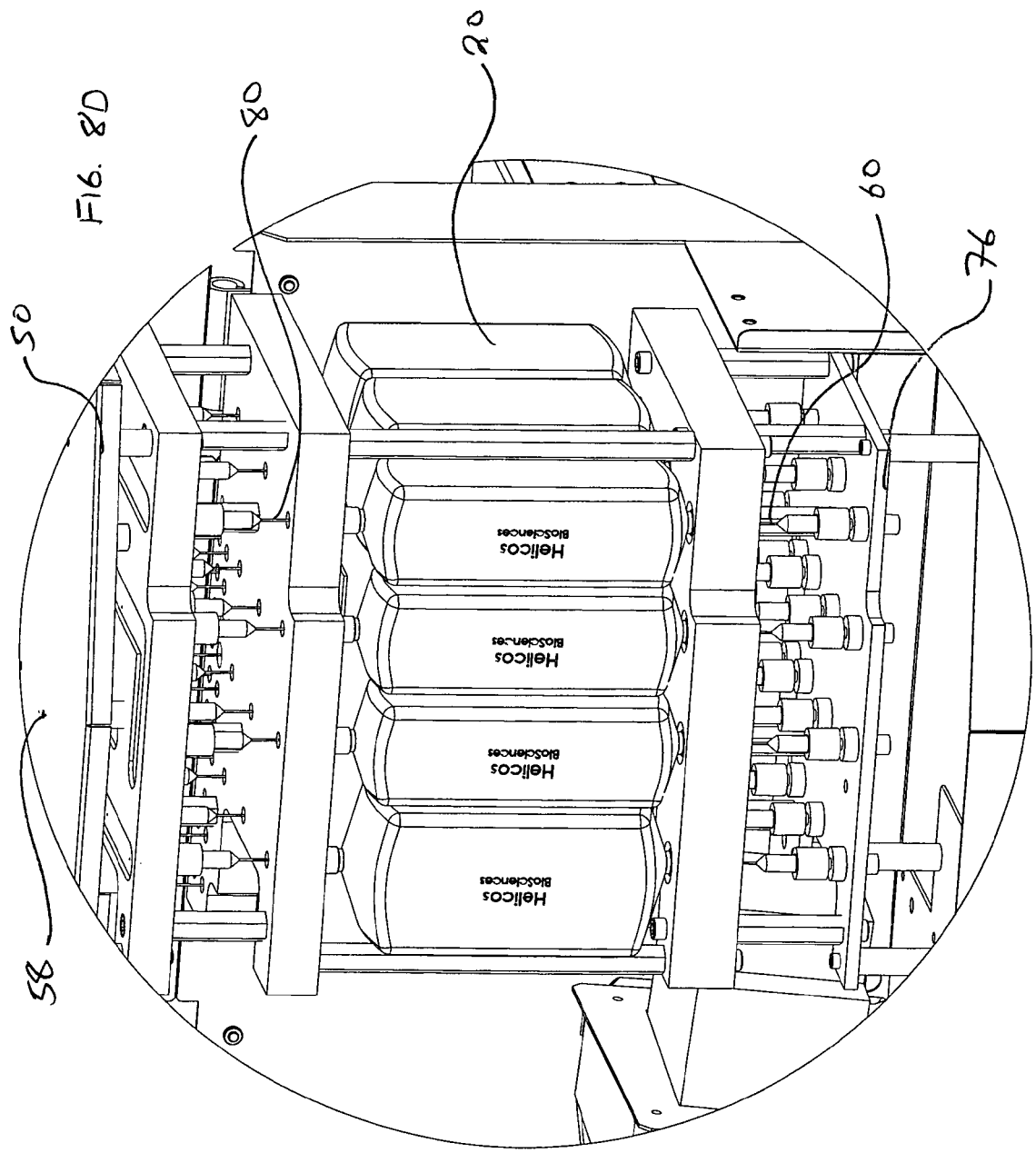
FIG. 8D is an enlarged schematic view of the needle and container assembly of FIG. 8C.

As shown in FIGS. 1, 2, and 5, all of the containers 20 are the same size and shape. Referring now to FIG. 7, a liquid storage apparatus 110 is shown with one container 130 larger than the other containers 120. The tops and bottoms of all of the containers 120, 130 are symmetrical having the same size and shape. The top and bottom cavities 142, 152 are also the same size and shape such that the containers 120, 130 can be loaded in either direction. This universal interface design allows a variety of different container sizes to be used in the liquid storage apparatus 110. In alternative embodiments, the tops and bottoms of the bottles 120, 130 and the top and bottom cavities 142, 152 are not all symmetrical (i.e., different sizes and shapes) which can prevent liquid reagents from being loaded in the wrong location.

As mentioned above, the liquid storage apparatus 110 of the present invention is designed for a wide variety of applications. In certain applications, such as single sequencing of DNA molecules, the liquid reagents can be very expensive. The user can customize the liquid storage apparatus 110 with larger containers for reagents that are used more frequently and smaller containers for those reagents that are used less frequently or in smaller quantities. Additionally, container cartridge assemblies can be designed for specific applications so that the liquid in each container of the assembly is used up at approximately the same time.

The liquid storage apparatus 10 can be a stand-alone apparatus that can be connected to a variety of lab equipment or it may be integrated into an individual piece of equipment. Referring now to FIG. 8A-8E, the frame 40 is integrated into a compartment of a single molecule sequencing device 90. To load the reagents, the user simply slides open the compartment 92 and opens the cover 94. Individual containers and/or cartridge assemblies are inserted into the appropriate locations. The liquid storage compartment 92 may be subdivided to store liquids at different temperatures.

The disclosed embodiments are exemplary. The invention is not limited by or only to the disclosed exemplary embodiments. Also, various changes to and combinations of the disclosed exemplary embodiments are possible and within this disclosure.

The invention claimed is:

1. A liquid storage apparatus for use in connection with microfluidic volume analyzing equipment, comprising:
   a plurality of containers, each container including a top pierceable septum and a bottom pierceable septum and each container including a liquid therewithin;
   a lower array of needles, each of the lower needles for penetrating the bottom pierceable septum of a different one of the containers, each lower needle including a passage through which the liquid in the pierced container flows out of the container; and an upper array of needles, each of the upper needles for penetrating the top pierceable septum of a different one of the containers, each upper needle including a passage through which a gas flows into the container to occupy space in the container created by the flow of the liquid out of the container.

2. The liquid storage apparatus of claim 1, wherein at least a subset of the plurality of containers are selectively secured together to form a cartridge assembly.

3. The liquid storage apparatus of claim 1, wherein the lower array of needles comprises Trocar needles.

4. The liquid storage apparatus of claim 1, wherein the upper array of needles comprise non-coring deflected tip needles.

5. The liquid storage apparatus of claim 1, further comprising a filter fluidly coupled to the upper array of needles.

6. The liquid storage apparatus of claim 1, wherein upper array of needles is fluidly coupled to an inert gas system.

7. The liquid storage apparatus of claim 1, further comprising a level sensor to determine when the liquid level falls below a predetermined level.

8. The liquid storage apparatus of claim 7, wherein the level sensor is an ultrasonic level sensor.

9. The liquid storage apparatus of claim 7, wherein the level sensor is an optical level sensor.

10. The liquid storage apparatus of claim 7, wherein the level sensor is a capacitance level sensor.

* * * * *